US00PP08276P

United States Patent [19]

Dehan

[11] Patent Number: Plant 8,276

[45] Date of Patent: Jun. 22, 1993

[54] IMPATIENS PLANT NAMED DANLIGHT

[75] Inventor: Klara Dehan, Holon, Israel

[73] Assignee: Danziger — "Dan" Flower Farm, Mishmar Hashiva, Israel

[21] Appl. No.: 743,440

[22] Filed: Aug. 9, 1991

[51] Int. Cl.[5] ..... A01H 5/00
[52] U.S. Cl. ..... Plt./87.6
[58] Field of Search ..... Plt./87.6

*Primary Examiner*—James R. Feyrer
*Attorney, Agent, or Firm*—Foley & Lardner

[57] ABSTRACT

A new cultivar of Impatiens plant named Danlight characterized by its medium to large bicolored flowers, the main background color of which light is red-purple, with a darker red-purple base and radial stripe; dark green foliage with purple venation, good branching and fast growth habit, and its floriferousness.

1 Drawing Sheet

The present invention relates to a new and distinctive cultivar of Impatiens plant, botanically known as Impatiens, and known by the cultivar name Danlight. Danlight was developed by me through controlled breeding by crossing the cultivar designated by breeding number U-21 as the female parent with the cultivar designated 68-46 as the male parent. Both parents are unreleased, proprietary lines.

Asexual reproduction of Danlight by cuttings taken by applicant at Mishmar Hashiva, Israel, has shown that the unique features of this new impatiens are stabilized and are reproduced true to type in successive propagations. The cuttings preferably comprise tip cuttings with at least one axillary bud, which is vegetative and not a flower bud.

The following characteristics distinguish the new Impatiens from both its parent varieties and other cultivated Impatiens of this type known and used in the floriculture industry:

1. Medium to large bi-colored flowers.
2. Petal color is light pink for main portion, with darker pink or red-purple at base, along radial center stripe, and, with certain petals, laterally of the stripe.
3. Dark green foliage with purple venation, thereby providing a pleasing contrast between flower and foliage.
4. Good branching and fast growth.
5. Very floriferous, having thirty or more simultaneously open flowers.

The accompanying color photographs illustrate the overall appearance of Danlight, showing the colors as true as it is reasonably possible to obtain in a colored reproductiton of this type. The photo at the top of the sheet is a top perspective view of blooms and foliage of a part of a plant of Danlight. The photo at the bottom of the sheet is a closeup view of a single flower.

The following is a detailed description of my new Impatiens cultivar based on plants produced under commercial practice during the winter in Mishmar Hashiva, Israel.

Color references are made to The Royal Horticultural Society Colour Chart except where general terms of ordinary dictionary significance are used.

Danlight can be generally compared to the cultivar Twilight, disclosed in U.S. Plant Pat. No. 5,869, with both cultivars having bicolored flowers. However, unlike Twilight, the foliage of Danlight is not variegated.

In addition, the flower color of Danlight is in the red-purple ranges, as opposed to the more orange-red shades of Twilight.

PARENTAGE:

*Male parent.*—68-46.

*Female parent.*—*U*-21.

Propagation:

A. *Type cutting.*—Leaves without flower buds.

B. *Time to initiate roots.*—8–10 days both at 25°–30° C. summer, and 20°–22° C. winter.

C. *Rooting habit.*—Good root initiation.

Plant description:

A. *Form.*—Compact, symetrically mounded medium size plant with dark green-red foliage.

B. *Habit of growth.*—Good branching and fast growth.

C. *Foliage description.*—(1) Size: 7.5–8.0 cm in length and 3.0–3.5 cm in width. (2) Shape: Generally oval, tip acute. (3) Margin: Finely serrated. (4) Color: Young foliage top side closest to 147A, underside 59A. Mature foliage top side closest to 137A, underside 59A. (5) Venation: Purple. (6) Branches: Purple-red in color.

Flowering description:

A. *Flowering habits.*—The flower opens vertically requiring approximately 3–4 days from bud to open flower; flowers continuously when temperatures are above approximately 10° C. and there are at least minimum levels of light.

B. *Natural flowering season.*—Natural flowering in the spring in moderate climates. In Israel and also other warm climates it will flower in the winter.

C. *Flower buds.*—Normal shape and development. Spurs up to 5.5 cm long on mature buds with throat originating from major sepal; the wide oval part of the spur is 1.0 cm by 0.8 cm and close to 59C in color; the long part is approximately 4.5 cm in length, almost straight, and green 145A in color.

D. *Flowers borne.*—Flower buds are presented at the tips of stems overlying the terminal whorls of leaves. At most stems, there are generally about 4–5 buds in different stages of maturity, and normally about 1–2 or more open blooms, as the plant reaches market stage. It takes about three.

Weeks from the initiation of the first bud until about thirty flowers are open at the same time.

E. *Quantity of flowers.*—Very floriferous; there are approximately 30 simultaneously open flowers after 14 weeks after planting.

F. *Petals.*—(1) Shape: Generally heart shaped. (2) Color: Top side when opening, main color 65D, with a 58C in a radial center stripe and at the base; 58C extends laterally of the center stripe in certain petals; underside main color in 49B with base and radiant stripes being approximately 41B; there is little or no fading on petal maturation. (3) Number of petals: Five, all similarly shaped. (4) Size of flowers: Approximately 5.0 cm in total diameter.

G. *Reproductive organs.*—(1) Stamens: One in number. (a) Anther color: Red and light yellow. (b) Pollen color: White. (2) Pistils: (a) Stigma: Cone shaped; light green in color in fused with purple. (b) Style: Green in color. (c) Ovaries: One in number; size 1–1.5 mm; green in color.

Disease resistance: Good to date.

I claim:

1. A New and distinct cultivar of Impatiens plant named Daylight, as illustrated and described.

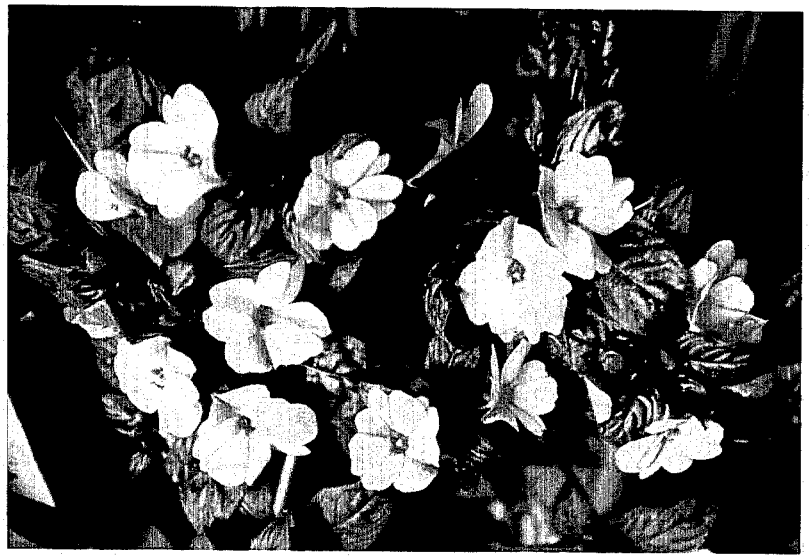
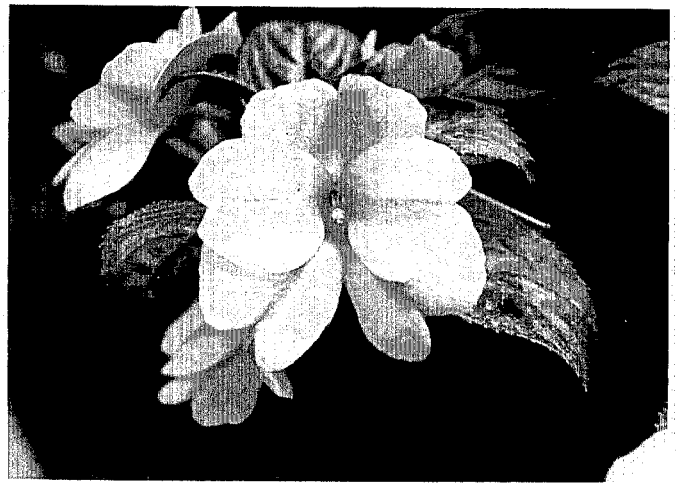

* * * * *